(12) United States Patent
Grevin et al.

(10) Patent No.: US 9,345,616 B2
(45) Date of Patent: May 24, 2016

(54) LIQUID DISPENSING DEVICE EQUIPPED WITH AN AIR DUCT

(75) Inventors: Guillaume Grevin, L'Isle d'Abeau (FR); Gaetan Painchaud, Francheville (FR); Thierry Decock, Lyons (FR); Xavier Julia, Villefontaine (FR)

(73) Assignee: NEMERA LA VERPILLIÈRE S.A.S. (FR)

( * ) Notice: Subject to any disclaimer, the term of this patent is extended or adjusted under 35 U.S.C. 154(b) by 232 days.

(21) Appl. No.: 14/115,271

(22) PCT Filed: Apr. 30, 2012

(86) PCT No.: PCT/FR2012/050962
§ 371 (c)(1),
(2), (4) Date: Nov. 1, 2013

(87) PCT Pub. No.: WO2012/150409
PCT Pub. Date: Nov. 8, 2012

(65) Prior Publication Data
US 2014/0074052 A1   Mar. 13, 2014

(30) Foreign Application Priority Data

May 4, 2011 (FR) ..................... 11 53834

(51) Int. Cl.
*A61F 9/00* (2006.01)
*B05B 11/00* (2006.01)
(Continued)

(52) U.S. Cl.
CPC ............ *A61F 9/0008* (2013.01); *A61M 11/008* (2014.02); *B05B 1/30* (2013.01);
(Continued)

(58) Field of Classification Search
CPC ....... A61F 9/0008; A61J 1/1443; A61J 1/145; A61J 1/1456; A61J 1/14; A61M 11/008; A61M 2210/0612; A61M 2210/0618; A61M 2210/0625; A61M 2210/0662; B05B 1/30; B05B 11/0021; B05B 11/0064; B05B 11/043; B05B 11/047; B05B 11/0016; B65D 47/18; B65D 47/32; Y10T 29/49826; B01D 53/22; B01D 2053/221; B01D 2053/222; B01D 53/228; G11B 33/1486; G11B 33/1446; G11B 33/1453; H01H 9/047
See application file for complete search history.

(56) References Cited

U.S. PATENT DOCUMENTS 3,722,697 A * 3/1973 Burke ................... A61M 5/165
                                                         210/451
4,127,131 A * 11/1978 Vaillancourt ......... A61M 5/165
                                                         210/448
(Continued)

FOREIGN PATENT DOCUMENTS

EP   0864371 A1   9/1998
FR   2810301 A1   12/2001
(Continued)

OTHER PUBLICATIONS

H Attaway, CH Gooding, MG Schmidt. Comparison of microporous and nonporous membrane bioreactor systems for the treatment of BTEX in vapor streams. Journal of Industrial Microbiology & Biotechnology (2002) 28, 245-251 D 2002. Nature Publishing Group. 1367-5435/02 www.nature.com/jim.*

(Continued)

*Primary Examiner* — Adam Marcetich
(74) *Attorney, Agent, or Firm* — St Onge Steward Johston and Reens LLC

(57) ABSTRACT

A liquid dispenser device including an air flow channel for passing air from the outside towards the inside of a liquid reservoir; a closure member for closing the air flow channel, the closure member being referred to as an "air diffuser member" and being made out of a non-porous polymer material that is permeable to air; and an isolator casing for isolating the diffuser member, the isolator casing being configured in such a manner that the diffuser member is not in contact with the liquid from the reservoir, the casing including an air flow element for passing air towards the inside of the reservoir.

16 Claims, 1 Drawing Sheet

Figure 1:
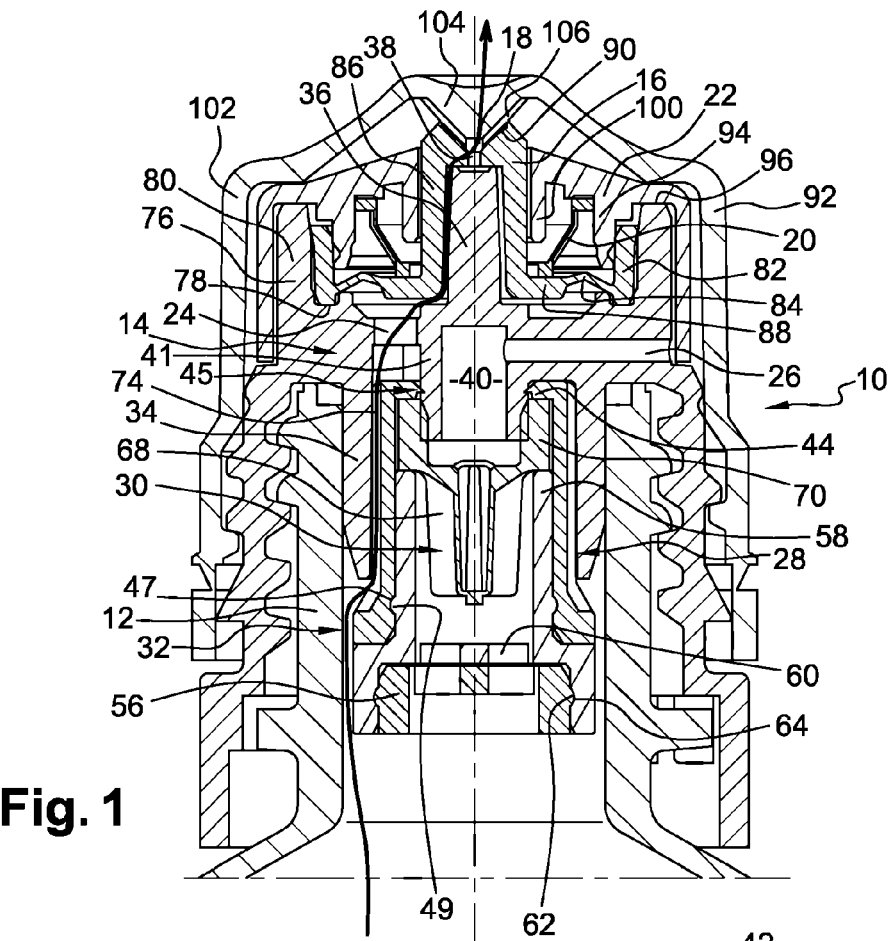

(51) Int. Cl.
*A61M 11/00* (2006.01)
*B05B 1/30* (2006.01)
*B05B 11/04* (2006.01)
*B65D 47/18* (2006.01)
*B65D 47/32* (2006.01)

(52) U.S. Cl.
CPC ........ *B05B 11/0016* (2013.01); *B05B 11/0021* (2013.01); *B05B 11/0064* (2013.01); *B05B 11/043* (2013.01); *B05B 11/047* (2013.01); *B65D 47/18* (2013.01); *B65D 47/32* (2013.01); *A61M 2210/0612* (2013.01); *A61M 2210/0618* (2013.01); *A61M 2210/0625* (2013.01); *A61M 2210/0662* (2013.01); *Y10T 29/49826* (2015.01)

(56) References Cited

U.S. PATENT DOCUMENTS

| | | | | |
|---|---|---|---|---|
| 4,472,276 A * | 9/1984 | Taylor | ................ | B01D 33/0006 210/236 |
| 4,512,771 A * | 4/1985 | Norton | ...................... | A61F 5/44 55/385.4 |
| 4,974,745 A * | 12/1990 | Jocham | .................. | H01H 9/047 220/202 |
| 5,108,474 A * | 4/1992 | Riedy | .................... | B01D 39/16 55/385.4 |
| 5,373,972 A | 12/1994 | Bystrom et al. | | |
| 5,428,123 A | 6/1995 | Ward et al. | | |
| 5,914,154 A * | 6/1999 | Nemser | ..................... | A61L 9/16 427/235 |
| 6,244,472 B1 | 6/2001 | Hennemann | | |
| 6,355,081 B1 * | 3/2002 | Wang | ................. | B01D 39/1623 428/391 |
| 8,986,266 B2 * | 3/2015 | Painchaud | ............ | A61F 9/0008 604/295 |
| 2002/0139095 A1 * | 10/2002 | Wang | ................. | B01D 39/1623 55/385.4 |
| 2002/0189455 A1 * | 12/2002 | Lamon | ................. | B01D 53/228 96/12 |
| 2003/0150882 A1 | 8/2003 | Bougamont et al. | | |
| 2003/0192826 A1 * | 10/2003 | Wang | ................. | B01D 19/0031 210/500.21 |
| 2005/0258282 A1 * | 11/2005 | Hagihara | .............. | B05B 11/047 239/571 |
| 2009/0294347 A1 | 12/2009 | Wochele et al. | | |
| 2010/0096416 A1 * | 4/2010 | Painchaud | ............ | B65D 47/18 222/496 |
| 2010/0107878 A1 * | 5/2010 | Crowder | ............ | B01D 19/0031 96/6 |
| 2011/0042315 A1 * | 2/2011 | Parnas | ................. | B01D 61/362 210/640 |
| 2011/0052900 A1 * | 3/2011 | Uno | ..................... | B01D 61/147 428/304.4 |
| 2011/0290112 A1 * | 12/2011 | Liu | ...................... | B01D 53/228 95/54 |

FOREIGN PATENT DOCUMENTS

WO 9201625 A1 2/1992
WO 9848943 A1 11/1998

OTHER PUBLICATIONS

International Search Report Application No. PCT/FR2012/050962 Completed: Jul. 12, 2012; Mailing Date: Jul. 20, 2012 3 pages.

* cited by examiner

LIQUID DISPENSING DEVICE EQUIPPED WITH AN AIR DUCT

FIELD OF THE INVENTION

The present invention relates to the field of dispensing liquid, in particular in the form of drops, in the pharmaceutical field, e.g. liquid for the eyes, the nose, the mouth, or the ears. More particularly, the invention relates to dispensing liquid without preservative, using a deformable reservoir with air intake.

The term "liquid" is used to designate a preparation that is non-solid and non-gaseous. It should be understood that the preparation may be liquid to a greater or lesser extent, depending on its viscosity, e.g. it may be pasty or semi-liquid.

BACKGROUND OF THE INVENTION

The current tendency is to provide preparations, in particular ophthalmic liquids, without preservative. The dispenser device must guarantee the sterility of the preparation throughout the working life of the bottle containing the liquid to be dispensed.

In an example, as described in document WO92/01625, such a dispenser device comprises a reservoir and a dispenser endpiece that is mounted on the reservoir and that is provided with a liquid dispenser orifice. The user applies pressure on the reservoir by deforming it, and, under the effect of the pressure, a drop is formed at the outlet of the dispenser orifice. Once the drop has been delivered, the user relaxes the pressure and the reservoir tends to return to its initial shape, thereby generating suction inside the reservoir. In order to compensate the suction and enable the reservoir to return to its initial shape, the endpiece of the device includes an air intake for admitting air into the reservoir. In order to ensure that the incoming air cannot contaminate the liquid contained in the reservoir, a hydrophobic filter is positioned in the air passage. The filter avoids micro-organisms and dust entering, while preventing liquid from exiting. The pore size of this type of filter is generally about 0.2 micrometers ($\mu m$), such that it prevents entry of most micro-organisms (e.g. *Brevundimonas Diminuta* bacteria which have a size of about 0.2 $\mu m$).

A problem with that type of device resides in the fact that it is very difficult to guarantee the integrity of used filters. In particular, it is difficult to test proper operation of the filter after it has been mounted on the endpiece, since the filter would then need to be tested in the presence of water or gas, thereby implying a risk of contamination or degradation during the test stage. Furthermore, none of the tests makes it possible to detect very small defects in the filter in a short period of time, compatible with manufacture at a very high rate.

OBJECTS AND SUMMARY OF THE INVENTION

A particular object of the present invention is to provide a liquid dispenser device with air intake that reliably guarantees the sterility of the content of a reservoir.

For this purpose, the invention provides a liquid dispenser device comprising:

an air flow channel for passing air from the outside towards the inside of a liquid reservoir;
a closure member for closing the air flow channel, said closure member being referred to as an "air diffuser member" and being made out of a non-porous polymer material that is permeable to air; and
an isolator casing for isolating the diffuser member, said isolator casing being configured in such a manner that the diffuser member is not in contact with the liquid from the reservoir, the casing including an air flow element for passing air towards the inside of the reservoir.

It is therefore proposed to perform the function of taking in air and blocking air-borne micro-organisms, not by an air filter, but by using the gas diffusing properties of certain materials. Thus, a member of a type other than a filter is used, namely a member made of non-porous polymer material. Such a member presents the advantage of passing non-contaminated air in a manner that is more reliable than a filter, which is porous by definition. With a non-porous member, it is easier to test whether there is any leak due to poor assembly or to a defective member.

The term "non-porous" material means a solid material, without any holes, that prevents the passage of particles such as bacteria, e.g. blocking the *Brevundimonas Diminuta* bacteria having a size of about 0.2 $\mu m$. The diffuser member differs from a filter. The non-porous material proposed for the air diffuser member is made up of a polymer that is used in its raw form, e.g. after being subjected merely to injection or to compression, while a porous material such as the material of a filter is made up of a polymer that has also been subjected to steps of generating pores or interstices, such as stretching the material or adding solvent to the polymer. Since the material is non-porous, it is liquidtight and does not allow particles such as dust or micro-organisms to pass therethrough. In contrast, the material is permeable to gases, in particular to air, as a result of it enabling molecules of the gases to be diffused. In other words, the non-porous material proposed above has gas permeability that allows air molecules to pass through an optionally cross-linked lattice of tangled molecular chains, so as to allow air to pass by diffusion through the diffuser member.

As a result of the material being non-porous, it should be observed that the passage of air through the member is a process that is slower than through a filter, which process may take several minutes, or several hours. For example, for a device that has enabled six drops to be dispensed, i.e. about 240 microliters ($\mu L$) of liquid, suction is almost compensated after twelve hours, i.e.

the pressure inside the bottle is then substantially equivalent to the pressure outside it. Such a return to a pressure that is close to the outside pressure might seem long, but the inventors of the invention have observed that this is not really troublesome, in particular when the volume of liquid dispensed at each administration is small, or when the time that passes between two successive administrations is long. This is the situation for example when dispensing drops of liquid, in particular drops of ophthalmic liquid.

Since the member does not include pores, it should be observed that there is no risk of clogging due to micro-organisms and dust accumulating in the pores.

This type of member of may be tested very easily after being mounted on the endpiece, without contaminating or degrading the member. For example, it is possible to apply air pressure to one side of the member and to measure the pressure on the other side after a few seconds. Since the process that makes it possible to balance the pressures on each side of the member is a process that takes several minutes or several hours, and not a few seconds, the time scale is not the same as for testing a filter. Also, at the one-second time scale, a non-defective member would not enable any loss of pressure to be detected, whereas a flagrant drop in pressure would be observed if the member were defective or poorly mounted on the endpiece. Such tests are easier, quicker, and more reliable than the tests that are usually performed on filters and that risk contaminating them or degrading them, or that provide relatively limited information if they are statistical tests on samples destroyed during the tests.

It should be observed that the air diffuser member is easy and inexpensive to manufacture. It thus differs from the hydrophobic filter that has the function of blocking air-borne micro-organisms, this filter possibly being costly to make, firstly in order to provide fine filtration, and secondly in order to ensure its integrity.

Furthermore, the isolator casing provided around the air diffuser member makes it possible to avoid the liquid for dispensing coming into contact with the diffuser member, and makes it possible to avoid the phenomena of sorption of molecules from the liquid occurring on the diffuser member, i.e. the phenomena of a molecule being absorbed in or adsorbed on a surface, or both. Sorption phenomena are particularly critical when the concentration of active principle in the solution is small, since they do not make it possible to guarantee that the required quantity of active principle will continue to be dispensed over time. If the active principle reacts in optionally-reversible manner with the material of the diffuser member when they are in contact, its concentration in the solution decreases and may become too small, thereby preventing the expected quantity of medication to be dispensed. Also, the isolator casing is particularly advantageous for liquids in which one of the components may interact with the air diffuser member, and in which the concentration of active principle in the solution is less than 1% by weight, or even less than 0.01% by weight, e.g. such as solutions based on prostaglandin or on a prostaglandin analog, in particular for treating glaucomas.

It should be understood that the isolator casing allows air to pass from the outside towards the inside of the reservoir by means of the air flow element, and prevents liquid from passing towards the inside of the casing.

The dispenser device may further comprise one or more of the following characteristics taken alone or in combination.

- The air flow element is a hydrophobic filter. This filter does not necessarily need to have the function of preventing the particles present in the air from entering into the reservoir, this function being provided by the diffuser member, but need only have the function of preventing liquid from penetrating into the casing. As a result of the presence of the diffuser member, it should be observed that the filter is of design that is simpler than that usually used for a hydrophobic filter since it does not need to have a pore size as small as 0.2 μm since it does not serve to prevent micro-organisms from penetrating into the reservoir. By way of example, it is possible to use a filter having a pore size that is greater than 1 μm, e.g. close to 10 μm.
- The air flow element is a check valve. Thus, it is possible to provide a simple air flow element.
- The casing includes a fastener piece for fastening the air flow element, the piece including a cylindrical skirt in which there is fitted a clamping ring for clamping the air flow element against the fastener piece. This makes it easy to assemble the air flow element, by pinching between the fastener piece and the clamping ring.
- The casing includes an end wall and a fastener piece for fastening the air flow element, the piece including a positioner abutment for positioning the diffuser member against the end wall of the casing. In this way, it is guaranteed that the diffuser member is suitably positioned against the end wall of the casing, and thus that any air entering the device passes through the diffuser member by diffusion. By way of example, the positioner abutment is carried by an annular wall of the fastener piece, which abutment is inserted into a sleeve defining the end wall of the casing, and comes to push the diffuser member against the end wall.
- The casing includes an outer surface that defines a liquid flow channel, at least in part. The liquid therefore does not enter into contact with the member.
- The liquid flow channel is a flowrate reducer channel. Thus, it is possible to create head losses within the liquid flow channel, e.g. by sudden changes of direction and/or of section, so as to provide better control over the quality of dispensing, in particular as a function of the viscosity of the liquid and of the size of drops that it is desired to dispense.
- The device includes a support in which the air flow channel is formed, and in which the casing provided with the diffuser member is fitted. For example, the support includes a central tubular cavity into which the air flow channel opens out, and inside which the casing provided with the member is fitted. Preferably, the support cooperates with an outer surface of the casing to define a liquid flow channel. In addition, the support is advantageously a support for a dispenser valve for dispensing the liquid.
- The diffuser member is provided with a plurality of portions in relief, so as to increase the surface area for passing air by diffusion.
- The polymer material of the diffuser member comprises a silicone rubber based elastomer. The gas permeability of this type of elastomer makes it possible to further enhance the air intake process.

The invention also provides a method of assembling a device as defined above, in which method the device includes a support, and the method comprises a pre-assembly step of assembling the diffuser member in the casing, then an assembly step of assembling the casing, provided with the diffuser member, on the support. This method of assembly is simple to implement, in particular because the pre-assembly of the member in the casing avoids any need to mount the diffuser member and the air flow element separately on the device.

BRIEF DESCRIPTION OF THE DRAWING

The invention can be better understood on reading the following description given merely by way of example, and with reference to the drawing, in which:

FIG. 1 is a diagrammatic section view of a liquid dispenser device in a first embodiment;

FIG. 2 is an exploded perspective view of the casing and of the diffuser member of the FIG. 1 device; and FIG. 3 is an exploded perspective view of a casing and of a diffuser member of a device in a second embodiment.

MORE DETAILED DESCRIPTION

FIG. 1 shows a liquid dispenser endpiece 10 for dispensing liquid in the form of drops, which endpiece is for mounting by screw-fastening on the neck of a reservoir 12. The reservoir 12 is a liquid storage reservoir, e.g. pharmaceutical liquid such as an ophthalmic liquid. The reservoir 12 is deformable in such a manner as to dispense liquid by squeezing the reservoir. More precisely, liquid is dispensed by a user applying pressure on the body of the reservoir 12, said body possibly presenting a certain amount of elasticity so as to return to its initial shape after pressure has been exerted by the user, thereby generating suction inside the reservoir 12.

In this embodiment, the dispenser endpiece 10 comprises: a support 14; a dispenser valve 16 that is provided with a dispenser orifice 18; return means 20 for returning the valve 16 against the support 14 in the blocking configuration, which return means are, in this embodiment, made up of a washer made of plastics material; and a cover 22. The endpiece 10 defines a liquid flow channel 24 for passing liquid from the reservoir 12 towards the dispenser orifice 18, shown by an arrow in FIG. 1, and an air flow channel 26 for passing air from the outside towards the inside of the reservoir 12. The channel 26 is closed by an assembly 28 including an air diffuser member 30 that is arranged in an isolator casing 32 for isolating the diffuser member 30.

In this embodiment, the support 14 includes an inner skirt 34 of tubular shape that extends upstream and that makes it possible to provide sealing between the reservoir 12 and the dispenser endpiece 10, and an outer skirt for fastening on the neck 12 of the reservoir, e.g. by screw-fastening.

It should be understood that the upstream direction and the downstream direction are defined relative to the flow direction of the liquid while it is being dispensed.

The support 14 also includes a central sealing portion 36 of substantially-cylindrical shape that extends downstream, away from the skirt 34. On its downstream end, the portion 36 carries a bearing surface 38 for the valve 16 for preventing liquid from passing in a blocking configuration. In this embodiment, the bearing surface 38 takes the shape of an annular bead.

In this embodiment, the support 14 defines the air flow channel 26 for passing air towards the inside of the reservoir 12. The channel 26, which opens out to a central cavity 40 of substantially-cylindrical shape, having an axis that coincides with the longitudinal axis of the device, is defined in part by an annular wall 41 of the support. At its proximal end, the cavity 40 receives the diffuser member 30. The air passage channel 26 is molded entirely in the support 14. It should be observed that the channel 26 may optionally include a plurality of sections of diameter that decreases on going away from the periphery of the support 14 and towards the center of the support 14, so as to facilitate molding operations and make the molding tools easier to make.

Figure 2:
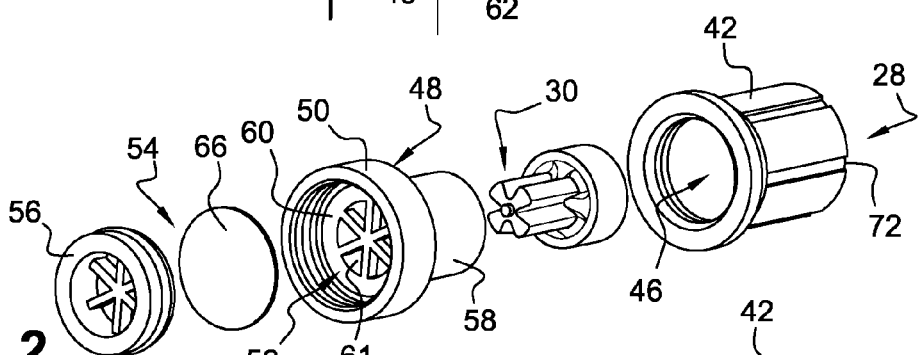

FIG. 2 shows an exploded perspective view of the assembly 28. In this embodiment, the casing 32 includes a sleeve 42 of substantially-tubular shape that is provided with an end wall 44 that includes a central orifice 45 that is substantially circular. The sleeve 42 defines a cavity 46 in which the diffuser member 30 comes to be housed.

The casing 32 also includes a fastener piece 48 that includes a transverse wall 60 that carries a first tubular skirt 50 that extends upstream and that co-operates with the wall 60 to define a cavity 52, and a second tubular skirt 58 that extends downstream, which second skirt is of diameter that is less than the diameter of the first skirt 50. The transverse wall 60 is perforated with at least one orifice 61 that makes it possible to pass air.

The second skirt 58 of the fastener piece 48 forms a positioner abutment for positioning the diffuser member 30 against the end wall 44 of the sleeve 42. Thus, the diffuser member 30 is pinched between the end wall 44 of the sleeve 42, and the second skirt 58 of the piece 48. The fastener piece 48 is held in place inside the sleeve 42 by co-operation between an annular bead 49 and an annular groove 47, carried respectively by an outer surface of the fastener piece 48 and by an inner surface of the sleeve 42.

The cavity 52 of the fastener piece 48 receives an air flow element 54 that is held by being clamped in the cavity 52 by a clamping ring 56 that is fitted in the first skirt 50. In the present embodiment, the air flow element 54 is clamped by co-operation between an annular bead 62 of the clamping ring 56 and an annular groove 64 that is carried by the inner surface of the first skirt 50 of the fastener piece 48. This method of clamping is simple and effective. However, the air flow element 54 could also be adhesively-bonded, molded, or welded, e.g. by ultrasonic welding, on the fastener piece 48.

In FIG. 2, the air flow element 54 is a hydrophobic filter 66 that allows air to pass, but prevents liquid from passing. The element 66 does not have an anti-bacterial or anti-particle barrier function since this function is provided by the air diffuser member 30. Thus, the only functions of the element 66 are to prevent liquid passing towards the air diffuser member, and to enable air to penetrate into the reservoir, there is no need for a blocking function for preventing micro-organisms that are present in the outside air from passing. The filter 66 may be in the form of a disk of small thickness.

The diffuser member 30 is made out of polymer material that is permeable to air, the material being non-porous, not allowing particles or micro-organisms to pass therethrough (e.g. bacteria of size greater than 0.2 μm), but allowing molecules to diffuse therethrough, such as the gas molecules contained in air. Thus, air passes through the diffuser member 30 by gas diffusing through the member 30. The polymer material comprises an elastomer material, namely, in this embodiment, a silicone rubber based elastomer, such as poly-di-methyl-siloxane (PDMS). The member 30 is generally cylindrical or conical in shape. It presents a central axis that coincides with the central axis of the endpiece 10, these axes corresponding to the liquid dispensing direction. More precisely, the member 30 comprises an "air diffuser" wall 68 of thickness that is relatively thin so as to encourage the exchange of gas, and a base comprising an annular fastener collar 70 for fastening on the endpiece 10, the collar 70 having a thickness that is relatively thick, and at least greater than the general thickness of the diffuser wall 68.

In this embodiment, the diffuser wall 68 includes a plurality of portions in relief that make it possible to increase the surface area for exchanging air between the inside and the outside of the reservoir 12, but without greatly increasing the bulkiness of the member 30. The portions in relief are formed in the wall in such a manner that it preserves its relatively thin thickness so as to allow air to pass therethrough. The portions in relief may also make it possible to stiffen the member 30, and thereby avoid using any reinforcement. In this embodiment, the portions in relief have a clover-shaped section.

The assembly 28, including the casing 32 and the diffuser member 30, is mounted as a single piece by clamping the collar 70 and the sleeve 42 mechanically on the outer surface of the annular wall 41 of the support 14. More precisely, the inside diameter of the collar 70 is slightly smaller than the outside diameter of the wall 41, such that the collar 70 is fastened on the wall 41 by radial clamping as a result of its springiness.

Optionally, it is also possible to provide mechanical fastener means for mechanically fastening the collar 70 on the wall 41, e.g. snap-fastener means such as an inner annular bead provided on the collar 70 snap-fastening in an annular groove provided on the outer surface of the wall 41. The central orifice 45 of the sleeve 42 has an inside diameter that is slightly smaller than the outside diameter of the wall 41, thereby making it possible to fasten the sleeve on the support in manner that is liquidtight.

By means of the casing 32 defined by several distinct parts, namely the sleeve 42, the fastener piece 48, the air flow element 54, and the fastener ring 56, the diffuser member is isolated completely from the liquid flow channel 24 once the liquid dispenser device 10 has been assembled. Thus, no phenomena of sorption of molecules from the liquid to be dispensed can occur on the air diffuser member 30. It should be understood that since the diffuser wall 68 of the member presents a surface area that is relatively large, it is advantageous to avoid any phenomena of sorption on the wall 68. This is even more important when the molecules of the active principle are at a low concentration in the solution, which is the situation in this embodiment, in which the liquid to be dispensed includes prostaglandins.

Furthermore, the casing 32 includes an outer surface that defines at least one liquid flow channel 24. Furthermore, in this embodiment, the liquid flow channel 24 also has a function of limiting the rate at which liquid flows. More precisely, on its outer annular surface, the sleeve 42 includes a plurality of channels 72, shown in particular in FIGS. 1 to 3, and co-operating with the inner surface of the skirt 34 of the support 14 to define liquid flowrate reducer channels 74. The channels 74 have a diameter that is relatively constricted so as to reduce the pressure of the liquid when the user squeezes the reservoir 12. In a variant, the channels 72 could present variations in direction or in section, or could even be helical in shape. Depending on the number and on the size of the channels 72 placed facing the inner surface of the skirt 34, the flowrate at which the liquid is able to leave can be made greater or smaller.

In addition, the support 14 includes a fastener portion 76 for fastening the dispenser valve 16 on the support 14. The portion 76 also acts as a fastener portion for fastening the cover 22 on the support 14. It includes an annular groove 78 that is defined at its periphery by an annular wall 80. On its inner periphery, the annular groove 78 is also defined by an annular rib that is formed on a substantially disk-shaped wall through which the channel 24 passes.

By co-operating with the support 14, the dispenser valve 16 may take up both a blocking configuration and a liquid flow configuration. In this embodiment, it is made out of an elastomer material. In another embodiment, only a portion of the valve 16 is made out of an elastomer material, the other portion being made out of a stiffer material against which the return means 20 can bear. The valve 16 includes a fastener portion 82 for fastening to the support 14, which fastener portion forms a skirt of a shape that is substantially tubular. The fastener portion 82 is connected to a substantially disk-shaped web 84 from which a substantially-cylindrical central portion 86 projects. The web 84 also includes a bearing seat 88 against which the return means 20 bear. The portion 86 defines an inner cavity of substantially-cylindrical shape that is complementary to the portion 36. The portion 36 and the cylindrical portion 86 are coaxial and co-operate with each other to define a portion of the liquid flow channel 24. The liquid flow channel 24 opens out to the dispenser orifice 18 that is formed in the downstream end of the valve 16, which dispenser orifice opens out to a drop-forming shape 90.

The cover 22 includes an annular fastener portion 92 for fastening on the support 14, and another annular portion 94 that is coaxial with the portion 92 so as to define a groove 96 in which the annular wall 80 is engaged. The cover 22 also includes a bearing seat 98 against which the return means 20 bear, which bearing seat is extended over its inner periphery by an annular wall 100 through which the portion 86 passes, which annular wall has a centering function for centering the portion 86 of the valve 16.

The device 10 also includes a removable cap 102 that includes a portion 104 of substantially conical shape that complements the drop-forming shape 90. The portion 104 makes it possible to avoid the non-dispensed liquid stagnating in the drop-forming shape 90 when the cap is mounted on the device. Furthermore, in its surface for coming into contact with the drop-forming shape 90, the portion 104 includes a plurality of channels 106 that encourage expelling any liquid from the shape 90, which liquid might otherwise stagnate therein, and there is no risk of the liquid being able to penetrate back into the device.

The operation of the FIG. 1 device is described below.

At rest, i.e. when no user is pressing on the reservoir 12, the valve 16 is in its liquid blocking configuration, i.e. it bears against the surface 38 as a result of it being fastened in permanent manner on the support 14, exerting resilient stress on the valve, and as a result of the pressure exerted by the return means 20.

When a user presses on the reservoir 12, a pressure is exerted on the fluid which flows into the liquid flow channel 24, and, in this embodiment, the flow reducer channel 74, it not being possible for a liquid to pass through the casing 32. While flowing in the channel 74, the flowrate of the fluid reduces as a result of head loss. Under the effect of pressure, the fluid deforms and lifts the valve 16 which then passes into its liquid flow configuration, the fluid flows between the valve 16 and the bearing surface 38, and then passes into the channel 18 and into the cavity 90 in the form of drops.

Once the drop has been dispensed, the user relaxes the pressure on the deformable reservoir 12, which tends to return to its initial shape, thereby generating suction inside the reservoir 12. The valve closes immediately under the action of the return force of the return means 20: therefore no liquid returns inside the device. The suction is compensated by an intake of outside air coming from the air flow channel 26 through the air diffuser member 30 that is air permeable. It should be observed that as a result of the material constituting the member 30 being non-porous, the passage of air through the member 30 is a process that takes several minutes, or even several hours, and not a few seconds.

Thus, taking, by way of example, a device that has a capacity of 12 milliliters (mL), filled with 10 mL of an ophthalmic solution and provided with an air-permeable member comprising PDMS having a permeability to oxygen of $1.4*10^{-13}$ $mol*m^{-1}*Pa^{-1}*s^{-1}$ (moles per meter per Pascal and per second), an exchange surface area of 90 square millimeters ($mm^2$), and a thickness of 0.4 millimeters (mm), dispensing six drops of solution under atmospheric pressure, i.e. 40*6=240 microliters of liquid, creates suction of about 95 millibars (mbar) that is almost compensated in twelve hours (more precisely, about 90 mbar is compensated after twelve hours have elapsed).

Given that the wall of the member 30 is not porous, the time taken for air to enter into the reservoir 12 is approximately the same regardless of whether or not the device is in its "head down" position. Air can then pass through the hydrophobic element 66 so as to compensate the suction created within the device as a result of a drop of liquid being dispensed. It should thus be understood that the factor that limits air intake is the gas permeability of the member 30 and not the hydrophobic element 66.

It should be observed that by means of the isolator casing 32, the member 30 does not come into contact with the liquid to be dispensed.

It should be observed that the member 30, being a separate part, may have a shape that varies as a function of the application, of the desired air intake time, and/or of the desired flowrate reduction. It is thus possible to manufacture batches comprising endpieces presenting the same valve 16, the same support 14, the same cover 18, but presenting a variety of members 30.

Assembly of the FIG. 1 device is described below.

In a first assembly step for assembling the assembly, the diffuser member 30 is placed in the cavity 46 of the sleeve 42, then the fastener piece 48 is inserted, being held by the bead 49 snap-fastening in the groove 47. The hydrophobic element 66 is then placed in the cavity 52 of the fastener piece 48, and it is clamped by means of the fastener ring 56 being snap-fastened in the first skirt 50.

The assembly 28 is then fitted onto the support 14 by force-fitting onto the annular wall 41 in a second assembly step.

By means of the abutment-forming second skirt 58 of the fastener piece 48, it is guaranteed that the diffuser member 30 is properly positioned in the cavity 40, and that any air coming from the outside does indeed pass, by diffusion, through the air diffuser wall 68 of the member 30 before entering into the device 10.

Figure 3:
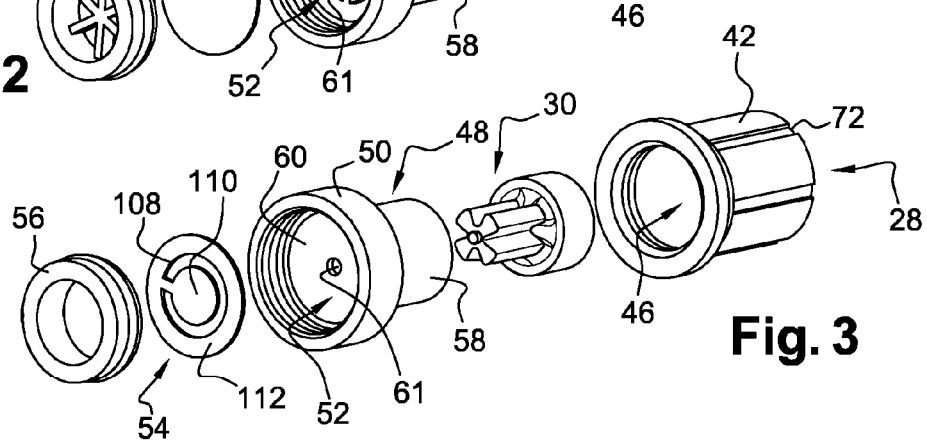

In the embodiment of the assembly 28 shown in FIG. 3, elements similar to elements of the first embodiment are identified by the same numerical references.

It should be observed that in this embodiment, the air flow element 54 is a non-return valve or check valve 108. By way of example, the check-valve 108 is formed by a central disk 110 made of plastics material that is connected to a ring 112 that is molded integrally with the disk 110. The ring 112 of the check-valve 108 is held clamped between the wall 60 of the fastener piece 48 and the clamping ring 56. The disk 110, at rest, takes up a liquid blocking configuration by co-operating with the wall 60, and when there is suction in the reservoir 12, it takes up an air flow configuration in which the disk 110 no longer co-operates with the wall 60 to close the orifice 61, but enables the air penetrating by diffusion through the wall 68 of the member 30 to enter into the reservoir. More precisely, the check-valve 108 functions with a resilient return force that is non-zero, which implies that it opens only when there exists a pressure difference between its upstream and downstream sides. Thus, when the pressure is identical on either side of the check-valve 108, said check-valve is flattened against its seat.

It should be observed that the check-valve 108 may well take on forms other than the form shown in FIG. 3. Any type of check valve may be envisaged, in particular a check-valve that is closed by the springiness of a material (e.g. a check-valve of a type often referred to as a "duck bill") and/or by the return force of a spring (e.g. a check-valve in the form of a pin or of a disk that is returned by a spring).

The remainder of the FIG. 3 device is similar to that of the above-described figures.

It should be observed that the invention is not limited to the embodiments described above.

In particular, the air diffuser member 30 could take on a shape different from the shape presented in the figures. For example, it could comprise a cylindrical or conical shaped wall 68 presenting a vertex that is closed by a disk-shaped surface, and an annular fastener collar 70 for fastening on the endpiece 10. In order to be stiffened, the wall could further include reinforcement splines that correspond to local increases in the thickness of the wall 68. In another variant, in place of or in addition to the reinforcement splines, the diffuser wall 68 could include a plurality of portions in relief that make it possible to increase the surface area for exchanging air between the inside and the outside of the reservoir 12, but without greatly increasing the bulkiness of the member 30.

The portions in relief are formed in the wall in such a manner that it preserves its relatively thin thickness so as to allow air to pass therethrough.

The return means for returning the valve 16 against its support are not essential, and they are not limited to a spring washer 20, as shown in FIG. 1. It is also possible to envisage using a spring, for example.

What is claimed is:

1. A liquid dispenser device, comprising:
    an air flow channel for passing air from the outside towards the inside of a liquid reservoir;
    an air diffuser member for closing the air flow channel, said air diffuser member being made out of a non-porous polymer material that is permeable to air;
    wherein the air diffuser member has one or more sections that protrude in relief from the air diffuser member;
    an isolator casing for isolating the diffuser member, said isolator casing being configured in such a manner that the diffuser member is not in contact with the liquid from the reservoir, the casing including an air flow element for passing air towards the inside of the reservoir;
    said air diffuser member being assembled in said isolator casing.

2. A device according to claim 1, wherein the air flow element is a hydrophobic filter or a check valve.

3. A device according to claim 1, wherein the casing includes a fastener piece for fastening the air flow element, the piece including a cylindrical skirt in which there is fitted a clamping ring for clamping the air flow element against the fastener piece.

4. A device according to claim 1, wherein the casing includes an end wall and a fastener piece for fastening the air flow element, the piece including a positioner abutment for positioning the diffuser member against the end wall of the casing.

5. A device according to claim 1, wherein the casing includes an outer surface that defines a liquid flow channel.

6. A device according to claim 5, wherein the liquid flow channel is a flowrate reducer channel.

7. A device according to claim 1, including a support in which the air flow channel is formed, and in which the casing provided with the diffuser member is fitted.

8. A device according to claim 1, wherein the diffuser member is provided with a plurality of sections in relief.

9. A device according to claim 1, wherein the polymer material of the diffuser member comprises a silicone rubber based elastomer.

10. A method of assembling a device according claim 1, wherein the device includes a support, and the method comprises a pre-assembly step of assembling the diffuser member in the casing, then an assembly step of assembling the casing, provided with the diffuser member, on the support.

11. A device according to claim 1, wherein the one or more sections that protrude in relief include clover shaped sections that protrude in relief in a thickness direction.

12. A device according to claim 1, wherein the one or more sections extend in a depth direction from the air diffuser member.

13. A device according to claim 1, wherein the air diffuser member is at least partially cylindrical or at least partially conical.

14. A liquid dispenser device, comprising:
    an air flow channel for passing air from the outside towards the inside of a liquid reservoir;
    an air diffuser member for closing the air flow channel, said air diffuser member being made out of a non-porous polymer material that is permeable to air, wherein the air diffuser member is at least partially cylindrical or at least partially conical;

an isolator casing for isolating the diffuser member, said isolator casing being configured in such a manner that the diffuser member is not in contact with the liquid from the reservoir, the casing including an air flow element for passing air towards the inside of the reservoir;

said air diffuser member being inside said isolator casing.

15. A device according to claim 14, wherein the air diffuser member has clover shaped sections that protrude in relief in a thickness direction.

16. A device according to claim 14, wherein the air diffuser member has one or more protruding sections that extend in a depth direction from the air diffuser member.

* * * * *